United States Patent [19]

Chida et al.

[11] Patent Number: 4,941,138

[45] Date of Patent: Jul. 10, 1990

[54] METHOD AND AN APPARATUS FOR MEASURING OPTICAL CHARACTERISTICS OF AN OPTICAL DISK

[75] Inventors: Naomichi Chida, Iruma; Akiyoshi Watanabe, Kodaira, both of Japan

[73] Assignee: Nakamichi Corporation, Kodaira, Japan

[21] Appl. No.: 360,388

[22] Filed: Jun. 2, 1989

Related U.S. Application Data

[63] Continuation of Ser. No. 109,774, Oct. 16, 1987, abandoned.

[30] Foreign Application Priority Data

| Oct. 21, 1986 [JP] | Japan | 61-250331 |
| Oct. 21, 1986 [JP] | Japan | 61-250332 |
| Oct. 21, 1986 [JP] | Japan | 61-250333 |
| Nov. 25, 1986 [JP] | Japan | 61-280525 |
| Nov. 25, 1986 [JP] | Japan | 61-280526 |

[51] Int. Cl.$^5$ ............................................. G11B 7/095
[52] U.S. Cl. ..................................... 369/44.41; 369/58
[58] Field of Search .................... 369/54, 58, 109, 110

[56] References Cited

U.S. PATENT DOCUMENTS

| 4,079,429 | 3/1978 | Travot et al. | 365/121 |
| 4,167,024 | 9/1979 | Hamisch | 369/110 |
| 4,443,873 | 4/1984 | Anthon | 369/110 |
| 4,551,819 | 11/1985 | Michl et al. | 365/121 |
| 4,660,187 | 4/1987 | Yoshino et al. | 360/114 |
| 4,691,308 | 9/1987 | Takagi et al. | 369/110 |

Primary Examiner—Donald McElheny, Jr.
Attorney, Agent, or Firm—Pearne, Gordon, McCoy & Granger

[57] ABSTRACT

This invention relates to a method and an apparatus for measuring optical characteristics such as Mueller matrices or double refraction of an optical disk in which a laser light which is focussed irradiates on an optical disk so that a tracking and a focus of the irradiation light is controlled based on the reflected light from the optical disk while polarization characteristics of the optical disk are measured based on the reflection light.

6 Claims, 5 Drawing Sheets

METHOD AND AN APPARATUS FOR MEASURING OPTICAL CHARACTERISTICS OF AN OPTICAL DISK

This is a continuation, of application Ser. No. 07/109,774 filed on Oct. 16, 1987 now abandoned.

BACKGROUND OF THE INVENTION

In prior arts, there has been used an ellipsometer or the like to measure optical characteristics of a substrate for an optical disk. In such a device, a known polarized bundle of parallel rays irradiates on a disk to be measured and the passed or reflected rays pass through an analyzer in a rotary condition whereby the optical characteristics of the disk are determined by measuring the polarization of the rays.

In practical cases of the disk used as a storage medium, the incident light rays of the disk are not in the form of parallel rays, but in the form of collected rays. Thus, it will be noted that it is very difficult to measure an effect by the optical characteristics of the disk taken on practical playback signals from the measurement result by the ellipsometer.

Since the diameter of the bundle of parallel rays of the ellipsometer cannot be as small as the width of the practical track formed on the disk, it is difficult to measure the effect of variation on the optical characteristics over the fine region which is taken on the practical playback signals. Furthermore, the ellipsometer disadvantageously has a large configuration in case that it is tried to improve the accuracy of the optical axis thereof and also has an adjustment made difficult when the disk to be measured is mounted with a longer time also taken for the adjustment.

SUMMARY OF THE INVENTION

Accordingly, it is a principal object of the invention to provide a method and/or an apparatus for more effectively measuring optical characteristics such as Mueller matrices or double refraction of a substrate such as one for an optical disk in practical use controlling a tracking and a focussing as storage medium.

It is another object of the invention to provide a method and/or an apparatus, for measuring optical characteristics of an optical disk in which the result of measurement is analyzed so that causes of various errors which occur when recorded or played back by the optical disk can be proved.

It is further object of the invention to provide a method and/or an apparatus for measuring optical characteristics of an optical disk in which various properties such as the property of a substrate for the optical disk as well as that of the optical disk can be checked.

In accordance with one aspect of the present invention, there is provided a method of measuring optical characteristics of a substrate for an optical disk comprising the steps of;

converting a laser light into at least one predetermined polarized light ray selectively;

collecting said polarized light ray into an irradiation light ray to be irradiated onto said optical disk;

controlling a tracking and a focussing of an irradiation point on said optical disk of said irradiation light ray based on a reflection light ray from said optical disk;

dividing said reflection light ray into at least three polarized components;

detecting the light quantity of each of said polarized components;

and measuring polarization characteristics of a substrate for said optical disk based on said light quantity.

In accordance with another aspect of the present invention, there is provided an apparatus for measuring Mueller matrices of a substrate for an optical disk comprising;

a laser light source to output laser light;

means to selectively convert said laser light into four predetermined polarizations of light rays;

means to collect said polarized light rays into an irradiation light ray to be irradiated on said optical disk;

tracking control means to control tracking of an irradiation point of said irradiation light ray based on a reflection light ray from said optical disk;

focussing control means to control a focus of said irradiation point based on said reflection light ray;

polarization component dividing means to divide said reflection light ray into four polarized components;

four light quantity detection means to detect the light quantity of each of said polarized components;

memory means to store said light quantity detected by said four light quantity detection means; and operational means to determine the Mueller matrices of said substrate for said optical disk based on said light quantity data whereby an operation is made based on sixteen light quantity data stored by said memory means corresponding to said laser irradiation light ray of four polarized components selected by said polarization means at the same irradiation position of said optical disk.

In accordance with another aspect of the present invention, there is provided an apparatus for measuring Mueller matrices of a substrate for an optical disk comprising;

a laser light source to output laser light;

means to selectively convert said laser light into four predetermined polarizations of light rays;

means to collect said polarized light rays into an irradiation light ray to be irradiated on said optical disk;

control information detecting means to detect errors in tracking and focussing of an irradiation point of said irradiation light ray based on a reflection light ray from said optical disk;

polarization component dividing means to divide said reflection light ray into four polarized component; and four light quantity detection means to detect the light quantities of said polarized components, respectively.

In accordance with another aspect of the present invention; there is provided an apparatus for measuring double refraction of a substrate for an optical disk comprising;

a laser light source to output laser light;

means to convert said laser light into a predetermined polarized light ray;

means to collect said polarized light ray into an irradiation light ray to be irradiated on said optical disk;

tracking control means to control tracking of an irradiation point of said irradiation light ray based on a reflection light ray from said optical disk;

focussing control means to control a focus of said irradiation point based on said reflection light ray;

polarization component dividing means to divide said reflection light ray into three different polarized components;

three light quantity detection means to detect the light quantity of said polarized components, respectively; and operational means to make a predetermined measurement based on said light quantity whereby at least one of an azimuth and a retardation of said substrate for said optical disk is measured based on three light quantity data detected by said three light quantity detection means at the same irradiation position of said optical disk.

In accordance with a further aspect of the present invention, there is provided an optical pickup apparatus for measuring double refraction of a substrate for an optical disk comprising;

a laser light source to output laser light;

means to convert said laser light into a predetermined polarized light ray;

means to collect said polarized light ray into an irradiation light ray to be irradiated on said optical disk;

control information detecting means to detect errors in tracking and focussing of an irradiation point of said irradiation light ray based on a reflection light ray from said optical disk;

polarization component dividing means to divide said reflection light ray into three polarized components; and three light quantity detection means to detect the light quantities of said polarized components, respectively.

BRIEF DESCRIPTION OF THE DRAWINGS

The above and other objects and features of the invention will be apparent from the description of the embodiments of the invention taken along with the accompanying drawings in which.

DETAILED DESCRIPTION OF PREFERRED EMBODIMENTS

In case that Mueller matrices of an optical element is measured, the optical characteristics of the optical element in the measurement system are expressed by Mueller matrices while the irradiated or detected light is expressed by Stokes parameters. In this case, there is a method in which irradiation light of four kinds of predetermined polarized light subsequently irradiates on the optical element while the Stokes parameters of the respective passed or reflected rays are measured to determine the Mueller matrices of the optical element. In order to measure the Stokes parameters a polarizer and a $\lambda/4$ plate are disposed on an optical path of the passed or reflected rays to a photodetector and the light quantity of the passed or reflected rays through the polarizer and the $\lambda/4$ plate is required to be detected by the photodetector under four different conditions of disposal.

A principle of the measurement will be described with reference to FIG. 4 hereinjustbelow.

Laser light, as an example of a coherent light source, in the form of linear polarized light from a laser 1 passes through a collimator lens 2 to form parallel rays and then through a $\lambda/4$ plate 3 to be made circularly polarized light Pa. The circularly polarized light Pa passes through a polarizer 4 and a $\lambda/4$ plate 5 having predetermined rotary angles $\theta_1$ and $\theta_2$ relative to a reference face, respectively. Proper selection of the rotary angles $\theta_1$ and $\theta_2$ causes circularly polarized light Pa to be deformed into an irradiation light Pb having a predetermined polarization which irradiates on a measured optical element 6. An output light Pc passing through or reflected from the measured optical element 6 passes through a $\lambda/4$ plate 7 and an analyzer 8 having rotary angles $\theta_3$ and $\theta_4$ relative to the reference face, respectively and thereafter the thus produced light Pd irradiates on a photodetector 9 to detect the light quantity.

In the aforementioned construction, how Stokes parameters of the output light Pc from the measured optical element 6 is measured will be described hereinjustbelow.

Suppose the Stokes parameters of the output light Pc and the incident light Pd are $\overline{Pc}$ and $\overline{Pd}$, respectively and that the Mueller matrices of the $\lambda/4$ plate 7 and the analyzer 8 are $\overline{M7}$ and $\overline{M8}$, respectively, the following expression can be obtained;

$$\overline{Pd} = \overline{M8} \cdot \overline{M7} \cdot \overline{Pc} \tag{1}$$

The light quantity detected by the photodetector 9 is one showing a first component of the Stokes parameters $\overline{Pd}$ of the incident light Pd. Supposed that the Stokes parameters of the incident light Pd on each of the following conditions are $\overline{Pd1}$, $\overline{Pd2}$, $\overline{Pd3}$ and $\overline{Pd4}$, respectively and that first components of the parameters are Pd1, Pd2, Pd3 and Pd4, respectively, wherein the rotary angles $\theta_3$ and $\theta_4$ of the $\lambda/4$ plate 7 and the analyzer 8 are zero, respectively, the expression (1) will become as follows;

$$Pd1 = \tfrac{1}{4} \begin{vmatrix} 1 & 1 & 0 & 0 \\ 1 & 1 & 0 & 0 \\ 0 & 0 & 0 & 0 \\ 0 & 0 & 0 & 0 \end{vmatrix} \begin{vmatrix} 1 & 0 & 0 & 0 \\ 0 & 1 & 0 & 0 \\ 0 & 0 & 0 & 1 \\ 0 & 0 & -1 & 0 \end{vmatrix} \begin{vmatrix} Pc_1 \\ Pc_2 \\ Pc_3 \\ Pc_4 \end{vmatrix} = \tfrac{1}{4} \begin{vmatrix} Pc_1 + Pc_2 \\ Pc_1 + Pc_2 \\ 0 \\ 0 \end{vmatrix}$$

and therefore, the expression Pd1 can be obtained as follows;

$$Pd1 = \tfrac{1}{4}(Pc_1 + Pc_2) \tag{2}$$

Similarly, in case of the rotary angle $\theta_3$ of the $\lambda/4$ plate 7 being zero while the rotary angle $\theta_4$ of the analyzer 8 is $\pi/2$, the expression Pd2 will become as follows;

$$Pd2 = \tfrac{1}{4}(Pc_1 - Pc_2) \tag{3}$$

Similarly, in case of the rotary angle $\theta_3$ of the $\lambda/4$ plate 7 being $\pi/4$ while the rotary angle $\theta_4$ of the analyzer 8 is $\pi/4$, the expression Pd3 will become as follows;

$$Pd3 = \tfrac{1}{2}(Pc_1 + Pc_3) \qquad (4)$$

Similarly, in case of the rotary angle $\theta_3$ of the $\lambda/4$ plate 7 being zero while the rotary angle $\theta_4$ of the analyzer 8 is $\pi/4$, the expression Pd4 will become as follows;

$$Pd4 = \tfrac{1}{2}(Pc_1 + Pc_4) \qquad (5)$$

As the expressions Pc1 through Pc4 are determined from the expressions (2) through (5), they will be expressed as follows;

$$\begin{aligned}
Pc_1 &= Pd1 + Pd2 \\
Pc_2 &= Pd1 - Pd2 \\
Pc_3 &= 2Pd3 - (Pd1 + Pd2) \\
Pc_4 &= 2Pd4 - (Pd1 + Pd2)
\end{aligned} \qquad (6)$$

Accordingly, it will be noted that the Stokes parameter $\overline{Pc}$ of the output light Pc from the measured optical element 6 can be determined by setting the rotary angles of the $\lambda/4$ plate 7 and the analyzer 8 as the aforementioned four conditions and detecting the amount of incident light Pd on the respective set conditions.

The Mueller matrices of the measured optical element 6 will be described hereinjustbelow;

Suppose that the Mueller matrices of the measured optical element 6 is $\overline{M6}$ while the Stokes parameter of the irradiation light Pb is $\overline{Pb}$, the following expression will be obtained;

$$\overline{Pc} = \overline{M6} \cdot \overline{Pb} \qquad (7)$$

The irradiation light Pb will be of desired Stokes parameter by selecting the rotary angles $\theta_1$ and $\theta_3$ of the polarizer 4 and the $\lambda/4$ plate 5 as shown hereinbelow. Suppose that the Stokes parameters of the output lights Pc obtained by irradiating these irradiation lights Pb on the measured optical element 6 are $\overline{Pc1}$, $\overline{Pc2}$, $\overline{Pc3}$ and $\overline{Pc4}$, respectively, the expression (7) will become as follows;

In case that the rotary angles $\theta_1$ and $\theta_2$ of the polarizer 4 and the $\lambda/4$ plate 5 are zero, respectively, which causes the irradiation lights Pb to be horizontal linear polarized lights, the expression (7) will become as follows;

$$\overline{Pc1} = \begin{vmatrix} Pc1_1 \\ Pc1_2 \\ Pc1_3 \\ Pc1_4 \end{vmatrix} = \begin{vmatrix} M6_{11} M6_{12} M6_{13} M6_{14} \\ M6_{21} M6_{22} M6_{23} M6_{24} \\ M6_{31} M6_{32} M6_{33} M6_{34} \\ M6_{41} M6_{42} M6_{43} M6_{44} \end{vmatrix} \begin{vmatrix} 1 \\ 1 \\ 0 \\ 0 \end{vmatrix} = \begin{vmatrix} M6_{11} + M6_{12} \\ M6_{21} + M6_{22} \\ M6_{31} + M6_{32} \\ M6_{41} + M6_{42} \end{vmatrix} \qquad (8)$$

Similarly, in case of the rotary angle $\theta_1$ being $\pi/2$, the rotary angle $\theta_2$ is zero, which causes the irradiation lights Pb to be vertical linear polarized lights, the expression (7) will become as follows;

$$\overline{Pc2} = \begin{vmatrix} Pc2_1 \\ Pc2_2 \\ Pc2_3 \\ Pc2_4 \end{vmatrix} = \begin{vmatrix} M6_{11} M6_{12} M6_{13} M6_{14} \\ M6_{21} M6_{22} M6_{23} M6_{24} \\ M6_{31} M6_{32} M6_{33} M6_{34} \\ M6_{41} M6_{42} M6_{43} M6_{44} \end{vmatrix} \begin{vmatrix} 1 \\ -1 \\ 0 \\ 0 \end{vmatrix} = \begin{vmatrix} M6_{11} - M6_{12} \\ M6_{21} - M6_{22} \\ M6_{31} - M6_{32} \\ M6_{41} - M6_{42} \end{vmatrix} \qquad (9)$$

Similarly, in case of the rotary angle $\theta_1$ being $\pi/4$, while the rotary angle $\theta_2$ is $\pi/4$, which causes the irradiation lights Pb to be linear polarized lights of $\pi/4$, the expression (7) will become as follows;

$$\overline{Pc3} = \begin{vmatrix} Pc3_1 \\ Pc3_2 \\ Pc3_3 \\ Pc3_4 \end{vmatrix} = \begin{vmatrix} M6_{11} M6_{12} M6_{13} M6_{14} \\ M6_{21} M6_{22} M6_{23} M6_{24} \\ M6_{31} M6_{32} M6_{33} M6_{34} \\ M6_{41} M6_{42} M6_{43} M6_{44} \end{vmatrix} \begin{vmatrix} 1 \\ 0 \\ 1 \\ 0 \end{vmatrix} = \begin{vmatrix} M6_{11} + M6_{13} \\ M6_{21} + M6_{23} \\ M6_{31} + M6_{33} \\ M6_{41} + M6_{43} \end{vmatrix} \qquad (10)$$

Similarly, in case of the rotary angle $\theta_1$ being zero, while the rotary angle $\theta_2$ is $\pi/4$, which causes the irradiation lights Pb to be right circular polarized lights, the expression (7) will become as follows;

$$\overline{Pc4} = \begin{vmatrix} Pc4_1 \\ Pc4_2 \\ Pc4_3 \\ Pc4_4 \end{vmatrix} = \begin{vmatrix} M6_{11} M6_{12} M6_{13} M6_{14} \\ M6_{21} M6_{22} M6_{23} M6_{24} \\ M6_{31} M6_{32} M6_{33} M6_{34} \\ M6_{41} M6_{42} M6_{43} M6_{44} \end{vmatrix} \begin{vmatrix} 1 \\ 0 \\ 0 \\ 1 \end{vmatrix} = \begin{vmatrix} M6_{11} + M6_{14} \\ M6_{21} + M6_{24} \\ M6_{31} + M6_{34} \\ M6_{41} + M6_{44} \end{vmatrix} \qquad (11)$$

The following expression will be obtained from the aforementioned expressions (8) through (11);

$$\begin{vmatrix} M6_{11} \\ M6_{21} \\ M6_{31} \\ M6_{41} \end{vmatrix} = \tfrac{1}{2}(\overline{Pc1} + \overline{Pc2})$$

$$\begin{vmatrix} M6_{12} \\ M6_{22} \\ M6_{32} \\ M6_{42} \end{vmatrix} = \tfrac{1}{2}(\overline{Pc1} - \overline{Pc2})$$

$$\begin{vmatrix} M6_{13} \\ M6_{23} \\ M6_{33} \\ M6_{43} \end{vmatrix} = \overline{Pc3} - \tfrac{1}{2}(\overline{Pc1} + \overline{Pc2})$$

$$\begin{vmatrix} M6_{14} \\ M6_{24} \\ M6_{34} \\ M6_{44} \end{vmatrix} = \overline{Pc4} - \tfrac{1}{2}(\overline{Pc1} + \overline{Pc2})$$

It will be noted that the Stokes parameters $\overline{Pc1}$ through $\overline{Pc4}$ of the irradiation lights Pc in the above expression can be determined by the aforementioned method.

Thus, it will be understood that the Mueller matrices of the measured optical element 6 can be measured by determining the respective Stokes parameters $\overline{Pc_1}$ through $\overline{Pc_4}$ of the output lights Pc from the measured optical element through sequential irradiation of the four kinds of polarized irradiation lights Pb on the measured optical element 6.

In this case, if the outline of the polarization characteristics of the measured optical element is previously known or if the parameter or parameters to be measured are limited, then the measurement will be able to be more easily made.

A principle of such a measurement will be described with reference to FIG. 8.

Laser light from a laser 40 passes through a collimator lens 41 to form parallel rays and then through a group of optical elements 42 comprising a λ/4 plate and a polarizer to be made an irradiation light Pe of desired polarization characteristics, which is irradiated on a measured optical element 43. Output light Pf passing through or reflected from the measured optical element 43 is divided by dividing mirrors $44_1$ and $44_2$ and passes through respective optical element groups $45_1$, $45_2$ and $45_3$ to produce incident lights Pg1, Pg2 and Pg3 which enter photodetectors $46_1$, $46_2$ and $46_3$, respectively for detecting the light quantity thereby.

In the aforementioned construction, suppose that Stokes parameters of the irradiation lights Pe and the incident lights Pg1, Pg2 and Pg3 are $\overline{Pe}$, $\overline{Pg1}$, $\overline{Pg2}$ and $\overline{Pg3}$, respectively, and that Mueller matrices of the measured optical element 43 and the optical element groups $45_1$, $45_2$ and $45_3$ are $\overline{M}$, $\overline{Ma}$, $\overline{Mb}$ and $\overline{Mc}$, the expressions $\overline{Pg1}$, $\overline{Pg2}$ and $\overline{Pg3}$ are as follows;

$$\overline{Pg1} = \overline{Ma} \cdot \overline{M} \cdot \overline{Pe} \quad (13)$$

$$\overline{Pg2} = \overline{Mb} \cdot \overline{M} \cdot \overline{Pe} \quad (14)$$

$$\overline{Pg3} = \overline{Mc} \cdot \overline{M} \cdot \overline{Pe} \quad (15)$$

The light quantity detected by the respective photodetectors $46_1$, $46_2$ and $46_3$ are one indicating a first component of the respective Stokes parameters $\overline{Pg1}$, $\overline{Pg2}$ and $\overline{Pg3}$. Suppose that the first components are $Pg1_1$, $Pg2_1$ and $Pg3_1$, respectively, and that first components of the respective Mueller matrices $\overline{Ma}$, $\overline{Mb}$ and $\overline{Mc}$ are (Ma1 Ma2 Ma3 Ma4), (Mb1 Mb2 Mb3 Mb4), (Mc1 Mc2 Mc3 Mc4), respectively, the following expression will be established.

$$\begin{vmatrix} Pg1_1 \\ Pg2_1 \\ Pg3_1 \end{vmatrix} = \begin{vmatrix} Ma_1 Ma_2 Ma_3 Ma_4 \\ Mb_1 Mb_2 Mb_3 Mb_4 \\ Mc_1 Mc_2 Mc_3 Mc_4 \end{vmatrix} \overline{M} \begin{vmatrix} Pe_1 \\ Pe_2 \\ Pe_3 \end{vmatrix} \quad (16)$$

Suppose that the measured optical element 43 is a linear phase element and that its azimuth θ is about zero, the Mueller matrices M' can be expressed as follows;

$$\overline{M'} = \begin{vmatrix} 1 & 0 & 0 & 0 \\ 0 & 1-(1-\cos\Delta)\sin^2 2\theta & (1-\cos\Delta)\sin 2\theta \cos 2\theta & -\sin\Delta\sin 2\theta \\ 0 & (1-\cos\Delta)\sin 2\theta \cos 2\theta & 1-(1-\cos\Delta)\sin^2 2\theta & \sin\Delta\cos 2\theta \\ 0 & \sin\Delta\sin 2\theta & -\sin\Delta\cos 2\theta & \cos\Delta \end{vmatrix}$$

In the expression, r designates transmittance or reflectance while Δ designates a retardation.

As the Mueller matrices $\overline{M'}$ is substituted into the expression (16), $$\begin{vmatrix} Pg1_1 \\ Pg2_1 \\ Pg3_1 \end{vmatrix} = r \begin{vmatrix} C_{11}C_{12}C_{13}C_{14}C_{15} \\ C_{21}C_{22}C_{23}C_{24}C_{25} \\ C_{31}C_{32}C_{33}C_{34}C_{35} \end{vmatrix} \begin{vmatrix} 1 \\ \theta(1-\cos\Delta) \\ \theta\sin\Delta \\ \cos\Delta \\ \sin\Delta \end{vmatrix} \quad (16)'$$

wherein $C_{11} = Ma_1 \cdot Pe_1 + Ma_2 \cdot Pe_2$ $C_{12} = 2(Ma_2 \cdot Pe_3 - Ma_3 \cdot Pe_2)$ $C_{13} = 2(Ma_2 \cdot Pe_4 + Ma_4 \cdot Pe_2)$ $C_{14} = -(Ma_3 \cdot Pe_3 + Ma_4 \cdot Pe_4)$ $C_{15} = Ma_3 \cdot Pe_4 - Ma_4 \cdot Pe_3$ Similarly, the expressions $C_{21}$ through $C_{25}$ and $C_{31}$ through $C_{35}$ are ones in which the "Mb" and "Mc" are substituted for "Ma" of the above expressions, respectively. Thus, the transmittance or reflectance r, the azimuth θ and the retardation Δ can be determined by caluculating the unknown values r, θ and Δ from the expression (16)', respectively.

A method of simplifing the calculation in which the expression (16)' is solved will be stated hereinjustbelow. To this end, the following conditions will be supposed.

$C_{11} \neq 0 \quad C_{12} \approx 0 \quad C_{13} \approx 0 \quad C_{14} \approx 0 \quad C_{15} \neq 0$ $C_{21} \neq 0 \quad C_{22} \approx 0 \quad C_{23} \neq 0 \quad C_{14} \approx 0 \quad C_{25} \approx 0$ $C_{31} \neq 0 \quad C_{32} \approx 0 \quad C_{33} \neq 0 \quad C_{34} \approx 0 \quad C_{35} \approx 0$ As the above conditions are substituted into the expression (16)', the following results are obstained;

$$Pg1_1 = r(C_{11} + C_{15} \sin\Delta) \quad (17)$$

$$Pg2_1 = r(C_{21} + C_{23}\theta \sin\Delta) \quad (18)$$

$$Pg3_1 = r(C_{31} + C_{33}\theta \sin\Delta) \quad (19)$$

As an example in which the above conditions are met is set the following expression;

$$\begin{vmatrix} Ma_1 Ma_2 Ma_3 Ma_4 \\ Mb_1 Mb_2 Mb_3 Mb_4 \\ Mc_1 Mc_2 Mc_3 Mc_4 \end{vmatrix} = \begin{vmatrix} 1 & 0 & 1 & 0 \\ 1 & -1 & 0 & 0 \\ 1 & 1 & 0 & 0 \end{vmatrix} \overline{Pe} = \begin{vmatrix} 1 \\ 0 \\ 0 \\ 1 \end{vmatrix}$$

In this case, the expressions (17) through (19) will become as follows;

$$Pg1_1 = r(1 + \sin\Delta) \quad (17)'$$

$$Pg2_1 = r(1 - 2\theta\sin\Delta) \quad (18)'$$

$$Pg3_1 = r(1 + 2\theta\sin\Delta) \quad (19)'$$

From the expressions (17)′ through (19)′ can be determined the transmittance or reflectance r, the azimuth $\theta$ and the retardation $\Delta$ as follows;

$$r = (Pg2_1 + Pg3_1)/2 \tag{20}$$

$$\sin \Delta = 2Pg1_1/(Pg2_1 + Pg3_1) - 1 \tag{21}$$

$$\theta = (Pg3_1 - Pg2_1)/2(Pg1_1 - Pg2_1 - Pg3_1) \tag{22}$$

Thus, it will be noted that they are more easily calculated.

As aforementioned, suppose that the measured optical element 43 is a linear phase element, the predetermined irradiation light Pe is irradiated on the measured optical element, through which or from which passes or is reflected the output light Pf. The output light Pf is divided into three light rays which pass through the three optical element groups $45_1$, $45_2$ and $45_3$ having three kinds of the Mueller matrices $\overline{Ma}$, $\overline{Mb}$ and $\overline{Mc}$, respectively to detect the respective light quantity. Thus, the transmittance or reflectance r, the azimuth $\theta$ and the retardation $\Delta$ can be determined by the calculation based on the obtained light quantity.

Furthermore, it will be noted that the calculation can be more easily made by setting the first components of the Mueller matrices $\overline{Ma}$, $\overline{Mb}$ and $\overline{Mc}$ of the optical element groups $45_1$, $45_2$ and $45_3$ and the Stokes parameter $\overline{Pe}$ of the irradiation light Pe at the aforementioned conditions.

This invention has been made based on the aforementioned principle. An embodiment of the invention in which Mueller matrices of an optical disk are measured will be described with reference to FIG. 1.

Figure 1:
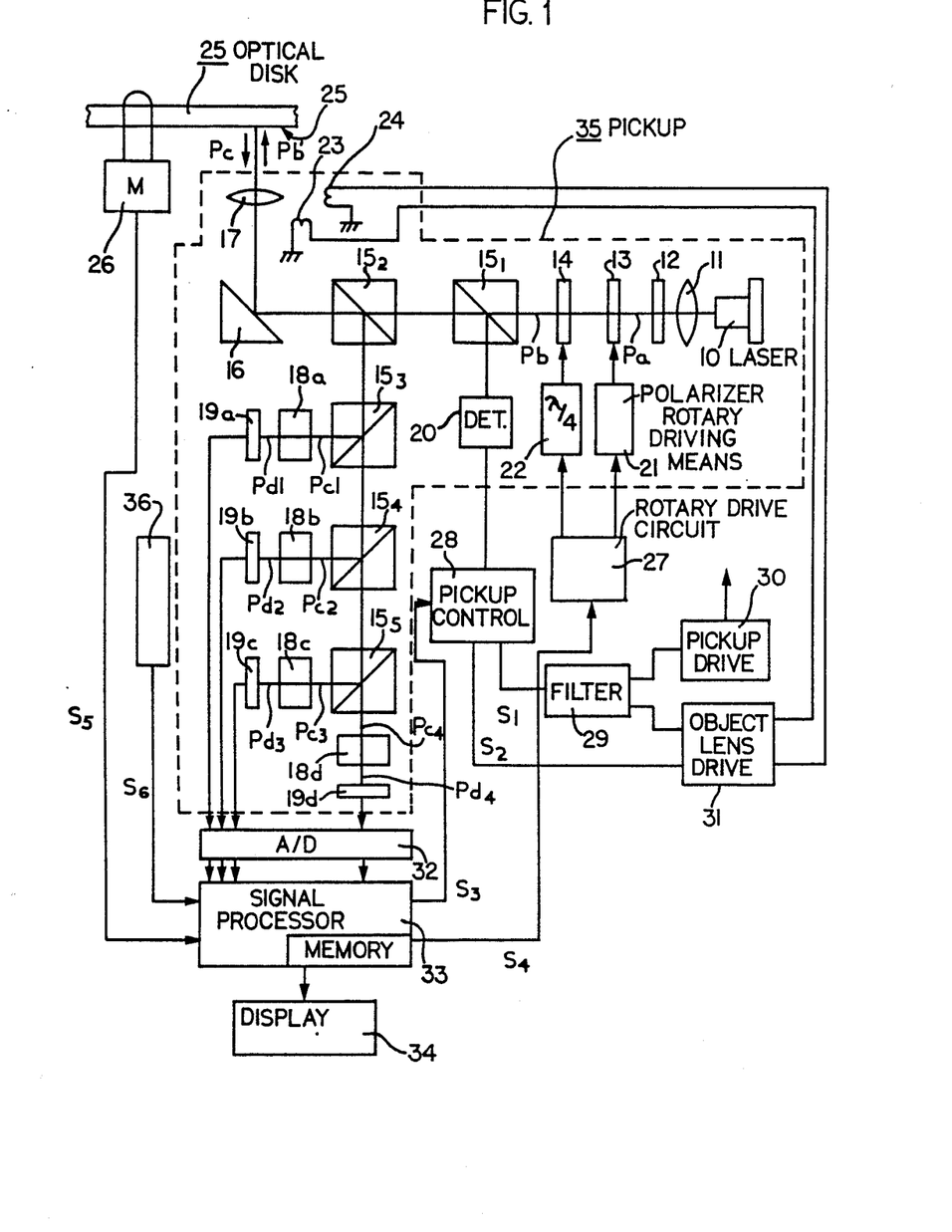
FIG. 1 is a schematic diagram of a system of the invention constructed in accordance with one embodiment of the invention.

A laser 10 is disposed in a pickup 35 which is illustrated by enclosing it with a dotted line. A laser light output from the laser 10 passes through a collimator lens 11 to be made parallel rays and then passes through a $\lambda/4$ plate 12 to be made a circularly polarized light Pa. The circularly polarized light Pa passes through a polarizer 13 and a $\lambda/4$ plate 14, which are held in the pickup so as to have respective rotary angles $\theta_5$ and $\theta_6$ variable relative to a reference face, to form a desired irradiation polarized light Pb, which thereafter passes through dividing mirrors $15_1$ and $15_2$, respectively to reach a full reflection mirror 16. After the irradiation light reflected by the full reflection mirror 16 passes through an objective lens 17 to be made a collected light, which is an actual irradiation light Pb' being irradiated on a reflection face $25_1$ of an optical disk 25 having a track formed thereon.

It will be noted from FIG. 1 that the objective lens 17 is disposed within the pickup 35 so that it can move in a radial direction of an irradiation point on the reflection face $25_1$ of the optical disk 25 in accordance with a tracking current flowing through a tracking coil 23 disposed near the objective lens 17 and its focus can be adjusted in accordance with a focussing current flowing through a focussing coil 24 disposed near the objective lens 17.

Figure 3:
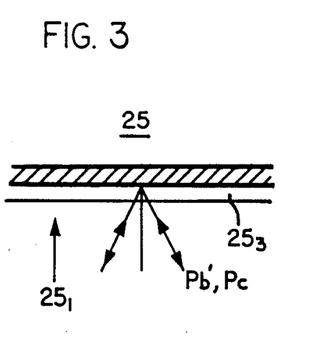
FIG. 3 is a cross sectional view of the optical disk of FIG. 2.

A reflected light Pc reflected by the reflection face $25_1$ of the optical disk 25 again passes through the objective lens 17 to be made parallel lights, which are reflected by the full reflection lens 16 to reach the dividing mirror $15_2$. The reflection face $25_1$ of the optical disk 25 is covered with a substrate $25_3$ of polycarbonate or the like as shown in FIG. 3. An optical effect such as double refraction which is produced on reflection of light tends to occur when the light passes through the substrate.

The light reflected by the dividing mirrors $15_2$ is divided by dividing mirrors $15_3$, $15_4$ and $15_5$ and then passes as measured reflection lights $Pc_1$, $Pc_2$, $Pc_3$ and $Pc_4$ through optical element groups 18a, 18b, 18c and 18d, respectively.

The optical element groups comprise a $\lambda/4$ plate and an analyzer having desired rotary angles set relative to a reference face, respectively. The optical element groups serve to optically treat with the measured reflected lights passing through and then supply them as incident lights $Pd_1$, $Pd_2$, $Pd_3$ and $Pd_4$ to photodetectors 19a, 19b, 19c and 19d, respectively.

The reflection light passing through the dividing mirror $15_2$ is reflected by the dividing mirror $15_1$ and enters a control information detector 20 for detecting a tracking information on irradiation points on the reflection face $25_1$ and a focussing information from the reflection light.

Within the pickup 35 are disposed polarizer rotary drive means 21 and $\lambda/4$ plate rotary drive means 22, which serve to set the polarizer 13 and the $\lambda/4$ plate 14 so as to have the desired rotary angles $\theta_5$ and $\theta_6$, respectively, in accordance with drive signals output from a rotary drive circuit 27 based on a rotary angle instruction signal S4 from a signal processor 33.

A spindle motor 26 serves to rotationally drive the optical disk 25 at a desired revolution by means of drive means not shown.

Light quantity signals detected by the respective photodetectors 19a through 19d are converted into digital signals by an analog-to-digital converter 32 and then input into the signal processor 33 where various operations are made. The signal processor 33 also receives a rotation information signal S5 from the spindle motor 26 to detect the rotation information of the optical disk 25 and receives a position signal S6 from a potentiometer 36 for detecting a motional position of the pickup 35 to detect the track position of the irradiation points. The signal processor 33 also serves to produce a track jumping signal S3 and a rotary angle instruction signal S4 which sets the rotary angles $\theta_5$ and $\theta_6$ of the polarizer 13 and the $\lambda/4$ plate 14 within the pickup 35.

A pickup control circuit 28 receives the tracking and focussing information signals from the control information detector 20 to output a tracking control signal S1 and a focus control signal S2 for controlling the tracking and focussing.

An objective lens drive circuit 31 receives the focus control signal S2 and a high-band frequency signal of the tracking control signal S1 selected by a filter 29 to supply drive currents to the focussing coil 24 and the tracking coil 23 within the pickup 35 in accordance with the input signals so as to drive the objective lens 17. A pickup drive circuit 30 receives a low-band frequency signal of the tracking control signal S1 selected by the filter 29 to drive pickup drive means, not shown, in accordance with the input signal so as to move the whole pickup 35 in a radial direction of the optical disk 25.

The pickup control circuit 28 also outputs the tracking control signal S1 based on the track jumping instruction signal S3 from the signal processor 33 to be able to move the track jumping of the irradiation points.

Since the focussing control, the tracking control and the track jumping control are conventionally made, the detail description will be omitted.

An operation of the invention will be described hereinjustbelow.

Although a relation between the irradiation light Pb which is an output light of the $\theta/4$ plate 14 and the actual irradiation light Pb' which is an output light of the objective lens 17 and a relation between the reflection light Pc from the reflection face $25_1$ of the optical disk 25 and the measured reflection light Pc$_1$ through Pc$_4$ which are the incident lights of the respective optical element groups 18a through 18d are different according to the optical characteristics of the dividing mirrors, the object lens 17 and the full reflection mirror 16 interposed therebetween, it is supposed that Pb is equal to Pb', Pc is equal to Pc$_1$, Pc$_2$, Pc$_3$, Pc$_4$ in order to simplify the illustration.

These set conditions will be enabled by inserting an optical element or elements of appropriate optical characteristics into a predetermined position of an optical path for correction. An equivalent correction will be enabled by a calculation in view of the differences of these characteristics, the explanation of which will be omitted.

The Stokes parameter $\overline{Pc}$ of the reflection light Pc is determined by the method using the expression (1).

In this case, the respective Mueller matrices of the $\lambda/4$ plate and the analyzer of the respective optical element groups 18a through 18d correspond to $\overline{M7}$ and $\overline{M8}$ of the expression (1). By setting the rotary angles of the $\lambda/4$ plate and the analyzer of the optical element group 18a at zero, respectively, similarly setting those of the optical element group 18b at zero and $\pi/2$, respectively, similarly setting those of the optical element group 18c at $\pi/4$, resectively, and similarly setting those of optical element group 18d at zero and $\pi/4$, respectively, the respective light quantities of the incident lights Pd$_1$ through Pd$_4$ detected by the photodetectors 19a through 19d correspond to Pd1 through Pd4 in the expressions (2) through (5). Accordingly, the Stokes parameter $\overline{Pc}$ of the reflection light Pc can be determined by making an operation of the expression (6).

The Mueller matrices of the reflection face $25_1$ of the optical disk can be measured by the method using the expression (7). In this case, the Mueller matrices of the irradiation position of the reflection face $25_1$ correspond to $\overline{M6}$ in the expression. The respective rotary angles $\theta_5$ and $\theta_6$ of the polarizer 13 and the $\lambda/4$ plate 14 are sequentially set as follows;

(1) $\theta_5=0$, $\theta_6=0$,
(2) $\theta_5=\pi/2$, $\theta_6=0$,
(3) $\theta_5=\lambda 4$, $\theta_6=\lambda/4$,
(4) $\theta_5=0$, $\theta_6=\lambda/4$.

Suppose that the respective Stokes parameters of the reflection lights Pc obtained by irradiating at the same irradiation position of the reflection face the respective irradiation lights Pb1 through Pb4 which are produced as the rotary angles $\theta_5$ and $\theta_6$ are set at the above values (1) through (4), respectively are $\overline{PC1}$ through $\overline{Pc4}$, they correspond to the respective Stokes parameters $\overline{Pc1}$ through $\overline{Pc4}$ in the above expressions (8) through (11).

We will describe an example of actual measurement hereinjustbelow.

Figure 2:
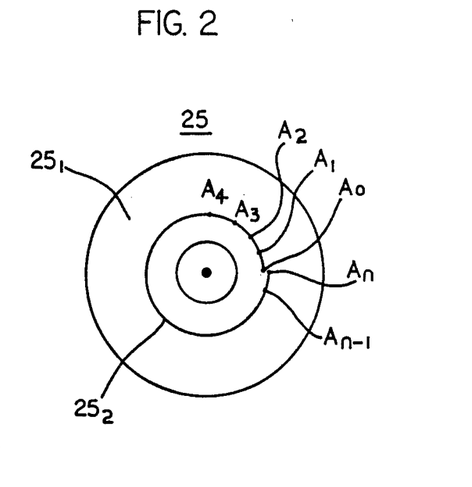
FIG. 2 is a plan view of an optical disk to be measured by the embodiment of the invention.

A spiral track $25_2$ is formed on the reflection face $25_1$ of the optical disk 25 at the predetermined region thereof. One round of the spiral track $25_2$ is shown in FIG. 2.

The signal processor 33 receives the rotary information signal S$_5$ and the position signal S$_6$, respectively to detect the position informations such as the track position and rotary angles of the irradiation points where the tracking is controlled along the track $25_2$ and as the irradiation point reaches the irradiation position A$_0$, the rotary angle instruction signal S$_4$ is output to set the rotary angles $\theta_5$ and $\theta_6$ of the analyzer 13 and the $\lambda/4$ plate 14 within the pickup 35 at zero, respectively. As the irradiation point reaches the respective irradiation position A$_1$ through A$_{n-1}$ corresponding to the predetermined rotary angles, the incident light quantity data detected by the respective photodetectors 19a through 19d at the respective irradiation positions are sequentially stored by a memory in the signal processor together with the position signals. When the irradiation point reaches the irradiation position A$_n$ having the same rotary angle as the irradiation position A$_0$, the track jumping instruction signal S$_3$ is output to jump the irradiation point by one track to again return the irradiation position to A$_0$. At the same time, the rotary angle instruction signal S$_4$ is output to set the rotary angles $\theta_5$ and $\theta_6$ of the polarizer 13 and the $\lambda/4$ plate 14 within the pickup 35 at $\pi/4$ and zero, respectively. Thus, as the irradiation point again reaches the respective irradiation positions A$_1$ through A$_{n-1}$, the incident light quantities detected by the photodetectors 19a through 19d at the respective positions thereof are stored together with the position informations thereof. Similarly, there are stored together with the position informations the incident light quantities at the irradiation positions A1 through A$_{n-1}$ when the rotary angles $\theta_5$ and $\theta_6$ of the polarizer 13 and the $\lambda/4$ plate 14 are set so that $\theta_5$ is $\pi/4$ while $\theta_6$ is $\pi/4$ and are set so that $\theta_5$ is 0 while $\theta_6$ is $\pi/4$.

After the above measurements are made, the signal processor 33 makes an operation based on the incident light quantity data to determine the Mueller matrices of the respective irradiation positions A$_1$ through A$_{n-1}$ of the optical disk.

For example, the mueller matrices of the irradiation position A$_1$ is determined as follows;

The signal processor 33 draws from the memory the incident light quantity data of the incident lights Pd$_1$ through Pd$_4$ when the rotary angles $\theta_5$ and $\theta_6$ of the polarizer 13 and the $\lambda/4$ plate 14 is set at the condition (1), the operation of the expression (6) is made to determine the Stokes parameter $\overline{Pc1}$ of the reflection light Pc. Similarly, the signal processor 33 sequentially draws from the memory the incident light quantity data of the respective incident lights when the rotary angles $\theta_5$ and $\theta_6$ are set at the conditions (2) through (4), respectively, the respective Stokes parameters $\overline{Pc2}$ through $\overline{Pc4}$ of the reflection light Pc are sequentially determined. Based on the Stokes parameters, the operation of the expression (12) is made to determine the Mueller matrices $\overline{M}_1$ of the irradiation position A$_1$. Similarly, the incident light quantity data corresponding to the respective irradiation positions A$_2$ through A$_{n-1}$ are sequentially drawn from the memory and then the operations of the expressions (6) and (12) are made to determine the Mueller matrices $\overline{M}_2$ through $\overline{M}_{n-1}$ at these positions.

A display 34 is provided to indicate the results of measurement. There are various methods of indication such as a digital indication of the result of measurement together with the track positions and the rotary angle informations and a graphic indication in which the optical disk face is colored based on the position informations and the results of measurement, for example, but we will omit the detailed explanation thereof.

Figure 5:
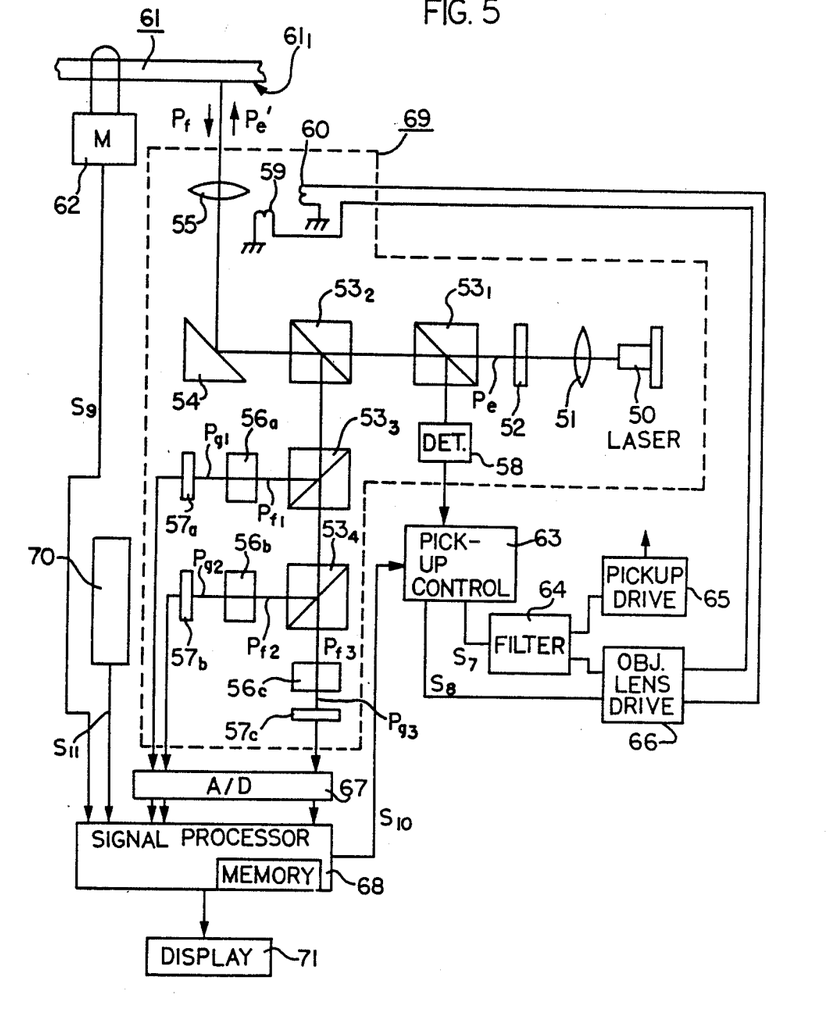
FIG. 5 is a schematic diagram of a system of the invention constructed in accordance with another embodiment of the invention.

FIG. 5 shows another embodiment of the invention in which the reflectance, the azimuth and the retardation of the optical disk where the optical characteristic is supposed to be a linear phase element are measured.

A laser 50 is disposed at a predetermined position within a pickup 69 which is illustrated by enclosing it with a dotted line. A laser light output from the laser 50 passes through a collimator lens 51 to be made parallel rays and then passes through an optical element groups 52 comprising a λ/4 plate and a polarizer to be made an irradiation light Pe having a desired polarization characteristic. The irradiation light Pe passes through dividing mirrors $53_1$ and $53_2$, respectively to reach a full reflection mirror 54. After the irradiation light reflected by the full reflection mirror 54 passes through an objective lens 55 to be made a collected light, which is an actual irradiation light Pe' being irradiated on a reflection face $61_1$, of an optical disk 61 having a track formed thereon.

The objective lens 55 is disposed within the pickup 69 so that it can move in a radial direction of an irradiation point on the reflection face of the optical disk 61 in accordance with a tracking current flowing through a tracking coil 59 disposed near the objective lens 55 and their focus can be adjusted in accordance with a focussing current flowing through a focussing coil 60 disposed near the objective lens 55.

A reflection light Pf reflected by the reflection face $61_1$ of the optical disk 61 again passes through the objective lens 55 to be made parallel rays, which are reflected by the full reflection lens 54 to reach the dividing mirror $53_2$. The reflection face $61_1$ of the optical disk 61 is covered with a subtrate $61_3$ of polycarbonate or the like as shown in FIG. 7. An optical effect such as double refraction which is produced on reflection of light tends to occur when the light passes through the substrate.

The light reflected by the dividing mirror $53_2$ is divided by dividing mirrors $53_3$ and $53_4$ and then passes as measured reflection lights $Pf_1$, $Pf_2$ and $Pf_3$ through optical element groups 56a, 56b and 56c, respectively. The optical element groups comprise a λ/4 plate and an analyzer and serve to optically treat with the measured reflected lights passing therethrough and then supply them as incident lights Pg1, Pg2 and Pg3 to photodetectors 57a, 57b and 57c, respectively.

The reflection light linearly passing through the dividing mirror $53_2$ is reflected by the dividing mirror $53_1$ and enters a control information detector 58 for detecting a tracking information on irradiation points on the reflection face $61_1$ and a fucussing information from the reflection lights.

A spindle motor 62 serves to rotationally drive the optical disk 61 at desired revolution by drive means not shown.

Light quantity signals detected by the respective photodetectors 57a through 57c are converted into digital signals by an analog-to-digital converter 67 and then input into a signal processor 68 where various operations are made. The signal processor 68 also receives a rotation information signal $S_9$ from the spindle motor 62 to detect the rotation information of the optical disk 61 and receives a position signal $S_{11}$ from a potentiometer 70 for detecting a motional position of the pickup 69 to detect the track position of the irradiation points and also serves to produce a track jumping signal $S_{10}$.

A pickup control circuit 63 receives the tracking and focussing information signals from the control information detector 58 to output a tracking control signal.$S_7$ and a focus control signal $S_8$ for controlling the tracking and focussing.

An objective lens drive circuit 66 receives the focus control signal $S_8$ and a high-band frequency signal of the tracking control signal $S_7$ selected by a filter 64 to supply drive currents to the focussing coil 60 and the tracking coil 59 within the pickup 69 in accordance with the input signals so as to drive the objective lens 55. A pickup drive circuit 65 receives a low-band frequency signal of the tracking control signal $S_7$ selected by the filter 64 to drive pickup drive means, not shown, in accordance with the input signal so as to move the whole pickup 69 in a radial direction of the optical disk 61.

The pickup control circuit 63 also outputs the tracking control signal $S_7$ based on the track jumping instruction signal $S_{10}$ from the signal processor 68 to be able to move the track jumping or the irradiation points.

Since the focussing control, the tracking control and the track jumping control are conventionally made, the detail description will be omitted.

An operation of the embodiment of FIG. 5 will be described hereinjustbelow.

Although a relation between the irradiation light Pe which is an output light of the optical elememt group 52 and the actual irradiation light Pe' which is an output light of the objective lens 55 and a relation between the reflection light Pf from the reflection face $61_1$ of the optical disk 61 and the measured reflection lights $Pf_1$ through $Pf_3$ which are the incident lights of the respective optical element groups 56a through 56c are different according to the optical characteristics of the dividing mirrors, the objective lens 55 and the full reflection mirror 54 interposed therebetween, it is supposed that Pe is equal to Pe', Pf is equal to $Pf_1$, $Pf_2$ and $Pf_3$, respectively in order to simplify the illustration thereof.

These setting conditions will be enabled by inserting an optical element or elements of appropriate optical characteristic into a predetermined position of an optical path for correction. An equivalent correction will be enabled by a calculation in view of the differences of these characteristics, the explanation of which will be omitted.

Under these setting conditions, an example of measurement of a reflectance r, an azimuth θ and a retardation Δ of the irradiation positions of the reflection face $61_1$ of the optical disk 61 will be described hereinjustbelow.

It is supposed that the Mueller matrices of the irradiation positions of the optical disk, the optical treating groups 56a, 56b and 56c are $\overline{M}$, $\overline{Ma}$, $\overline{Mb}$ and $\overline{Mc}$ and the first components of the respective Mueller matrices $\overline{Ma}$, $\overline{Mb}$ and $\overline{Mc}$ are (Ma1 Ma2 Ma3 Ma4). (Mb1 Mb2 Mb3 Mb4) and (Mc1 Mc2 Mc3 Mc4), respectively.

It is supposed that the light quantities of the incident lights detected by the respective photodetectors 57a, 57b and 57c are $Pg1_1$, $Pg2_1$ and $Pg3_1$, respectively and the Mueller matrices of the reflection face $61_1$ of the optical disk which is a linear phase element is $\overline{M}'$.

Figures 6, 7, 8:
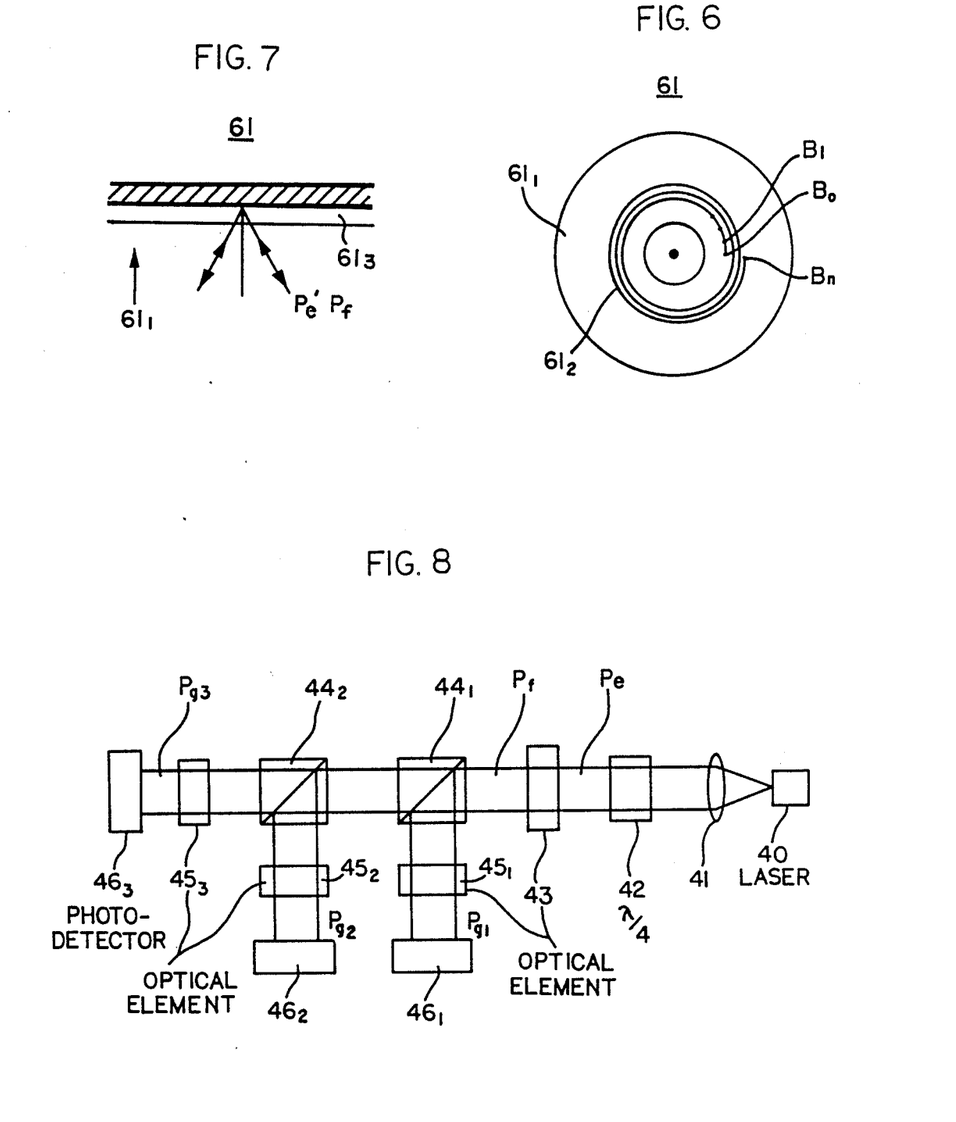
FIG. 6 is a plan view of an optical disk to be measured by the embodiment of FIG. 5.
FIG. 7 is a cross sectional view of the optical disk of FIG. 6.
FIG. 8 illustrates a principle of the embodiment of FIG. 5.

A spiral track $61_2$ is formed on the reflection face $61_1$ of the optical disk 61 at the predetermined area thereof and is partially shown in FIG. 6.

The signal processor 68 receives the rotary information signal $S_9$ and the position signal $S_{11}$, respectively, to detect the position informations such as the rotary angle and the track position of the irradiation points where the tracking is controlled along the track $61_2$. The measurement begins after the track jumping instruction signal $S_{11}$ is output so that the irradiation point may move to the desired irradiation position of the reflection face $61_1$ such as the irradiation position $B_0$ of FIg. 6, for example. As the irradiation point reaches the respective irradiation positions $B_1$ through $B_n$ corresponding to the preset rottary angle, the incident light quantity data detected by the photodetectors 57a through 57c at the respective positions thereof are sequentially stored together with the position informations thereof by memory within the signal processor 68.

After the aforementioned measurement, the signal processor 68 makes an operation based on the stored incident light quantity data stored to measure the reflectance r, an azimuth $\theta$ and a retardation $\Delta$ of the irradiation positions B1 through Bn of the optical disk.

For example, when the reflectance r, the azimuth $\theta$ and the ratardation $\Delta$ of the irradiation positions $B_1$ are to be measured, the incident light quantity data corresponding to this is to be drawn from the memory and then the expression (16)' is to be solved. As aforementioned, the expression can be more easily solved by setting the first components of the Mueller matrices of the respective optical element groups 56a, 56b and 56c and the Stokes parameter $\overline{Pe}$ of the irradiation light Pe as follows;

$$\begin{vmatrix} Ma1 & Ma2 & Ma3 & Ma4 \\ Mb1 & Mb2 & Mb3 & Mb4 \\ Mc1 & Mc2 & Mc3 & Mc4 \end{vmatrix} = \begin{vmatrix} 1 & 0 & 1 & 0 \\ 1 & -1 & 1 & 0 \\ 1 & 1 & 0 & 0 \end{vmatrix}, Pe = \begin{vmatrix} 1 \\ 0 \\ 0 \\ 1 \end{vmatrix}$$

Similarly, from the memory are sequentially drawn the incident light quantity data of the respective incident lights corresponding to the irradiation positions B1 through Bn and then the operations of the expressions (20) through (22) are made to determine the reflectance r, the azimuth $\theta$ and the retardation $\Delta$ at these positions.

A display 71 is provided to indicate the results of measurement. There are various methods of indication such as a digital indication of the result of measurement together with the track positions and the rotary angle informations and a graphic indication in which the optical disk face is colored based on the position informations and the results of measurement, for example, but we will omit the detailed explanation thereof.

Figure 9:
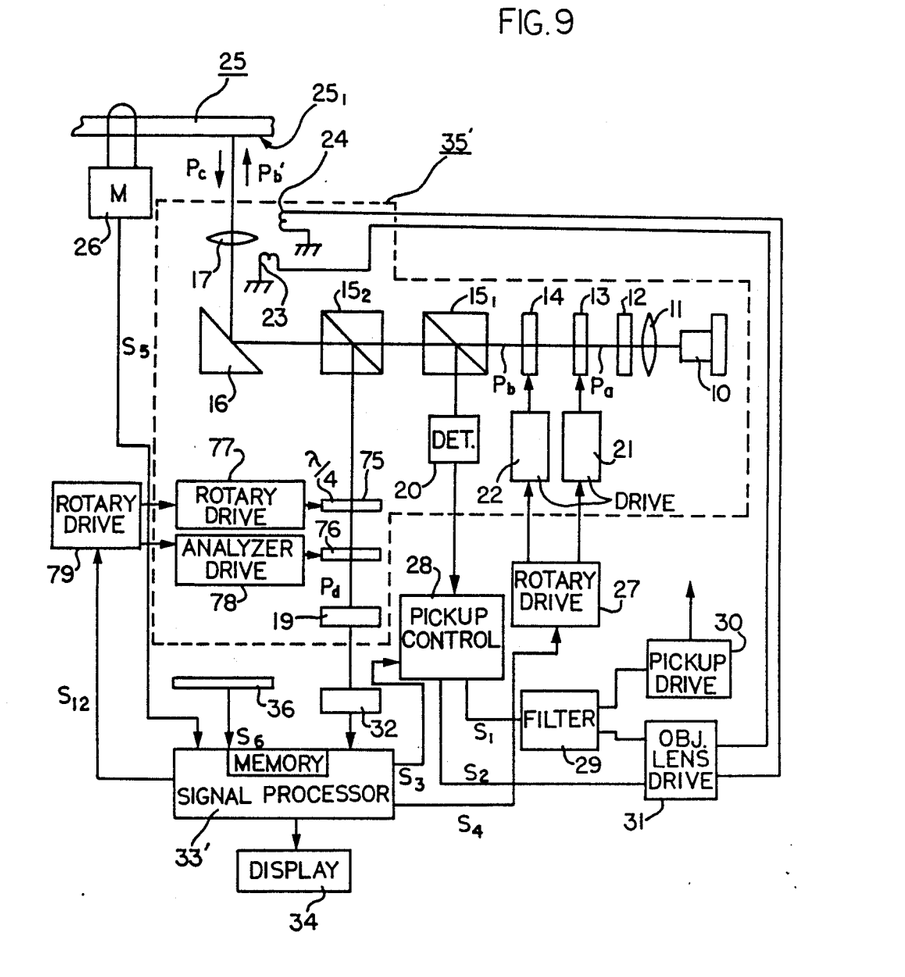
FIG. 9 is a system of the invention constructed in further embodiment of the invention.

FIG. 9 shows further embodiment of the invention. In the embodiment of FIG. 9, there are provided a $\lambda/4$ plate 75 and an analyzer 76 held within a pickup 35' so that respective rotary angles $\theta_7$ and $\theta_8$ of the elements are variable relative to the reference face in place of the optical element groups 18a through 18d having a $\lambda/4$ plate and an analyzer set at the aforementioned conditions and the dividing mirrors $15_3$ through $15_5$ in the embodiment of FIG. 1. The same reference numerals designate the same components.

There are provided within the pickup 35 a $\lambda/4$ plate rotary drive means 77 and an analyzer rotary drive means 78 which serve to set the $\lambda/4$ plate 75 and the analyzer 76 at the desired rotary angles $\theta_7$ and $\theta_8$ by a driving signal from a rotary drive means 79 in accordance with the rotary angle instruction signals $S_{12}$ from the signal processor 33'.

Accordingly, when the Stokes parameters of the reflection light Pc are to be determined, the rotary angles ($\theta_7$ and $\theta_8$) are sequentially set at (0, 0), (0, $\pi/2$), ($\pi/4$, $\pi/4$) and (0, $\pi/4$), respectively. There are sequentially detected by the photodetector 19 the light quantities Pd1 through Pd4 of the incident light Pd on the aforementioned set conditions, on which the expression (6) is solved to measure the Stokes parameters of the reflection light Pc.

It will be noted that since the light quantity has to be detected four times at the identical irradiation position upon the same irradiation light for detecting the light quantity in the embodiment of FIG. 9, a measurement time in the embodiment of FIG. 9 will be required at least four times as fast as the embodiment of FIG. 1.

It will be apparent from those skilled in the art that the embodiment of FIG. 5 may be modified by using an apparatuus comprising a $\lambda/4$ plate and an analzyer held within a pickup so that respective rotary angles of the elements are variable relative to the reference face in place of the optical element groups 56a through 56c and the dividing mirrors $53_3$ and $53_4$.

Although, in the embodiment of FIG. 1, the Mueller matrices of one round of the track at the sequential irradiation positions thereof are measured, the sequence of mesurement is never limited thereto. The irradiation light having four kinds of aforementioned polarization characteristics may irradiate on the same irradiation position of the track and then the Mueller matrices can be measured by detecting the light quantities by the respective photodetectors. Thus, it will be noted that the light quantities may be measured by various methods.

Furthermore, the construction of the polarizer 13 held in a rotatable manner within the pickup is never limited thereto and may be arranged by using a Faraday element having a polarization face rotatably driven by voltage in place of the $\lambda/4$ plate 12 and the polarizer 13 of FIG. 1.

A principle of measurement of Mueller matrices of a measured optical element 6 of FIG. 4 will now be described. A polarizer 4 and a $\lambda/4$ plate 3 are sequentially set so as to be disposed based on four types of conditions defined by rotary angles and an irradiation light Pb is supposed to be a polarized light peculiar to the respective disposal conditions. Therefore, four types of polarized light sequentially irradiate on the measured optical element 6. When each of four types of the polarized light sequentially irradiate on the measured optical element 6, four types of Stokes parameter of respective output lights Pc are measured, respectively, which are sequentially generated by passing the polarized light through the measured optical element 6 as shown in FIG. 4 or by reflecting the polarized light on the measured optical element 6. The Mueller matrices of the measured optical element can be measured from the four types of Stokes parameters. One Stokes parameter of the output lights Pc can be obtained by sequentially detecting by a photodetector 9 respevtive light quantities when a $\lambda/4$ plate 7 and an analyzer 8 are sequentially so set as to be disposed based on four types of conditions and then determining the Stokes parameter from the thus detected four light quantities. It will be noted that sixteen light quantities to be detected are necessary for obtaining the Mueller matrices of the measured optical element 6.

Figure 4:
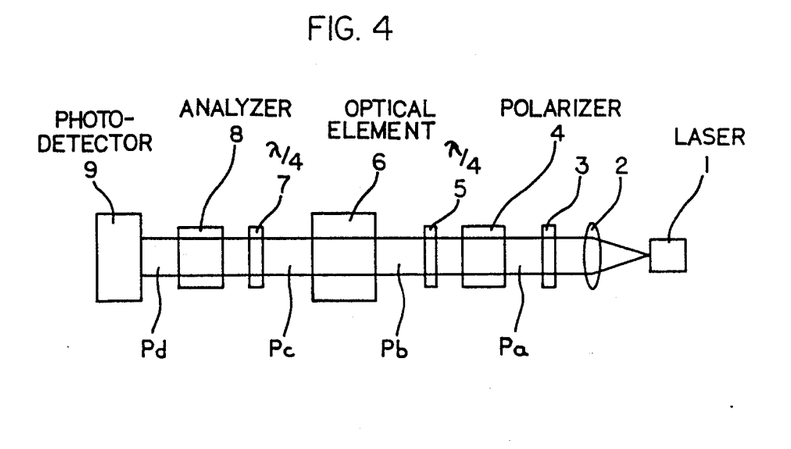
FIG. 4 illustrates a principle of the embodiment of FIG. 1.

In comparing the embodiment of FIG. 1 with the principle of FIG. 4, a polarizer 13 and $\lambda/4$ plate 14 of FIG. 1 correspond to the polarizer 4 and the $\lambda/4$ plate 5 of FIG. 4, respectively. Accordingly, the polarizer 13 and the λ/4 plate 14 are sequentially set to be at four rotary positions by respective rotary drive means 21 and 22 so that the irradiation light Pb sequentially becomes four types of polarized light.

The λ/4 plate 7 and the analyzer 8 of FIG. 4 sequentially set so as to be disposed in four types of conditions correspond to four optical element groups 18a, 18b, 18c and 18d of FIG. 1 each comprising the λ/4 plate and the analyzer.

The four optical elements 18a, 18b, 18c and 18d of FIG. 1 are stationarily disposed so as simultaneously to meet different one of the four disposal conditions, respectively, while in FIG. 4 the λ/4 plate 7 and the analyzer 8 are sequentially so set as to be disposed in four kinds of conditions. The measured reflected lights Pc$_1$, Pc$_2$, Pc$_3$ and Pc$_4$ are ones obtained by dividing the reflected light from the mirror 15$_2$ which corresponds to the reflected light Pc of FIG. 4 by dividing mirrors 15$_3$, 15$_4$, and 15$_5$ of FIG. 1, respectively and the following expression is supposed:

$$Pc = Pc_1 = Pc_2 = Pc_3 = Pc_4$$

It will be understood that while, in FIG. 4, the λ/4 plate 7 and the analyzer 8 are sequentially so set as to be disposed in four types of conditions and four types of light quantities are sequentially detected, the construction of FIG. 1 allows four types of light quantities to be simultaneously detected.

It should be noted that in the construction of FIG. 9, the λ/4 plate 75 and the analyzer 76 are sequentially so set as to be disposed in four types of conditions by being driven by rotary drive means 77 and 78, respectively, which is substantially identical to that of FIG. 4.

Next, a principle of measurement of an azimuth θ, a retardation Δ and a reflectance r of a measured optical element 43 of FIG. 8 will be described later. Please note that the measured optical element 43 is supposed to be a linear phase element.

In this case, an optical element group 42 comprising a λ/4 plate and a polarizer irradiates an irradiation light Pe of predetermined polarization characteristic on the measured optical element 43. When the irradiation light Pe irradiates on the optical element, an output light Pf obtained by passing the irradiation light Pe through the measured optical element 43 or by reflecting the irradiation light Pe on the measured optical element 43 is divided into three components of light and respective light quantities are detected through optical element groups 45$_1$, 45$_2$ and 45$_3$ having predetermined Mueller matrices by photodetectors 46$_1$, 46$_2$ and 46$_3$, respectively. The azimuth θ, the retardation Δ and the reflectance r of the measured optical element 43 can be obtained by making a calculation based on the thus detected light quantities. The specification describes how the optical element groups 42, 45$_1$, 45$_2$ and 45$_3$ should be set.

In comparing an embodiment of FIG. 5 with the principle of FIG. 8, it will be noted that the optical element groups 52, 56a, 56b and 56c of FIG. 5 correspond to the optical element groups 42, 45$_1$, 45$_2$ and 45$_3$ of FIG. 8, respectively.

As aforementioned, the principle of measurement of Mueller matrices of the measured optical element is described by the specification with reference to FIG. 4 and the embodiments of its principle are described with reference to FIGS. 1 and 9 while the principle of measurement of the azimuth θ, the retardation Δ and the reflectance r of the measured optical element is described with reference to FIG. 8 and the embodiment of its principle is described with reference to FIG. 5.

DESCRIPTION OF OPTICAL CHARACTERISTICS

"Mueller matrices" means matrices indicating the optical characteristics of an optical element in which the relation between an incident light entering one optical element and a light passing through the optical element or reflected thereby can be expressed by the expressions (1) and (7) in the specification when their characteristics are expressed by the Stokes parameters as indicated in the aforementioned expressions (1) and (7). Thus, it will be noted that if the Mueller matrix of one optical element is known, what characteristic a light obtained by reflecting the light irradiating on the optical element therefrom or passing it through the optical element has can be forecast.

Similarly, if an azimuth θ, a retardation Δ and a reflectance r of a measured optical element is known, what characteristic a light obtained by reflecting the light irradiating on the optical element therefrom or passing it through the optical element has can be forecast.

OBJECT OF THE INVENTION

As shown in FIG. 3, a light irradiating on an optical disk 25 is reflected by a reflecting face 25$_1$, covered with a substrate 25$_3$, but the light passes through the substrate 25$_3$. The invention has the feature that Mueller matrices, an azimuth θ, a retardation Δ and a reflectance r of an optical disk mainly determined by the substrate from the relation between the irradiation light and the reflected light can be measured while the optical disk is practically used, that is when the irradiation light is collective light and is subject to focussing and tracking.

Therefore, the invention does not have the object of writing signals on the optical disk or reading out signals on the optical disk.

While some preferred embodiment of the invention have been illustrated and described with reference to the accompanyiong drawings, it will be apparent to those skilled in the art that they are by way of examples, and that various changes and modifications may be made without departing from the spirit and scope of the invention, which is intended to be defined only by the appended claims.

What is claimed is:

1. A method of measuring optical characteristics of a substrate for an optical disk comprising the steps of;
   converting a laser light into at least one predetermined polarized light ray selectively;
   collecting said polarized light ray into an irradiation light ray to be irradiated onto said optical disk;
   controlling a tracking and a focussing of an irradiation point on said optical disk of said irradiation light ray based on a reflection light ray from said optical disk;
   dividing said reflection light ray into at least three polarized components;
   detecting the light quantity of each of said polarized components;
   and measuring polarization characteristics of a substrate for said optical disk based on said light quantity.

2. An apparatus for measuring Mueller matrices of a substrate for an optical disk comprising;
   a laser light source to output laser light;
   means to selectively convert said laser light into four predetermined polarizations of light rays;
   means to collect said polarized light rays into an irradiation light ray to be irradiated on said optical disk;
   tracking control means to control tracking of an irradiation point of said irradiation light ray based on a reflection light ray from said optical disk;
   focussing control means to control a focus of said irradiation point based on said reflection light ray;
   polarization component dividing means to divide said reflection light ray into four polarized components;
   four light quantity detection means to detect the light quantity of each of said polarized components;
   memory means to store said light quantity detected by said four light quantity detection means; and
   operational means to determine the Mueller matrices of said substrate for said optical disk based on said light quantity data whereby an operation is made based on sixteen light quantity data stored by said memory means corresponding to said laser irradiation light ray of four polarized components selected by said polarization means at the same irradiation position of said optical disk.

3. An apparatus for measuring Mueller matrices of a substrate for an optical disk as set forth in claim 2, wherein said polarization component dividing means comprises dividing mirrors to divide said reflection light ray into four optical paths on ends of which said four light quantity detecting means are disposed, respectively, and four different optical element groups disposed on said four optical paths, respectively, to detect four different polarization components from said reflection light ray, respectively.

4. An optical pickup apparatus for measuring Mueller matrices of a substrate for an optical disk comprising;
   a laser light source to output laser light;
   means to selectively convert said laser light into four predetermined polarizations of light rays;
   means to collect said polarized light rays into an irradiation light ray to be irradiated on said optical disk;
   control information detecting means to detect errors in tracking and focussing of an irradiation point of said irradiation light ray based on a reflection light ray from said optical disk;
   polarization component dividing means to divide said reflection light ray into four polarized components; and
   four light quantity detection means to detect the light quantities of said polarized components, respectively.

5. An apparatus for measuring double refraction of a substrate for an optical disk comprising;
   a laser light source to output laser light;
   means to convert said laser light into a predetermined polarized light ray;
   means to collect said polarized light ray into an irradiation light ray to be irradiated on said optical disk;
   tracking control means to control tracking of an irradiation point of said irradiation light ray based on a reflection light ray from said optical disk;
   focussing control means to control a focus of said irradiation point based on said refection light ray;
   polarization component dividing means to divide said reflection light ray into three different polarized components;
   three light quantity detection means to detect the light quantity of said polarized components, respectively; and
   operational means to make a predetermined measurement based on said light quantity whereby at least one of an azimuth and a retardation of said substrate for said optical disk is measured based on three light quantity data detected by said three light quantity detection means at the same irradiation position of said optical disk.

6. An optical pickup apparatus for measuring double refraction of a substrate for an optical disk comprising;
   a laser light source to output laser light;
   means to convert said laser light into a predetermined polarized light ray;
   means to collect said polarized light ray into an irradiation light ray to be irradiated on said optical disk;
   control information detecting means to detect errors in tracking and focussing of an irradiation point of said irradiation light ray based on a reflection light ray from said optical disk;
   polarization component dividing means to divide said reflection light ray into three polarized components; and
   three light quantity detection means to detect the light quantities of said polarized components, respectively.

* * * * *